United States Patent [19]
Stevenson et al.

[11] Patent Number: 6,068,850
[45] Date of Patent: May 30, 2000

[54] AQUEOUS FORMULATIONS OF PEPTIDES

[75] Inventors: Cynthia L. Stevenson, Mountain View; Sally A. Tao, San Jose; Steven J. Prestrelski, Mountain View; James B. Eckenhoff, deceased, late of Los Altos, by Bonnie J. Eckenhoff, executrix; Jeremy C. Wright, Los Altos; John J. Leonard, Jr., Cupertino, all of Calif.

[73] Assignee: Alza Corporation, Calif.

[21] Appl. No.: 09/248,286

[22] Filed: Feb. 11, 1999

Related U.S. Application Data

[63] Continuation of application No. 08/874,694, Jun. 13, 1997, Pat. No. 5,916,582.
[60] Provisional application No. 60/021,199, Jul. 3, 1996.

[51] Int. Cl.[7] ..................................................... A61F 2/02
[52] U.S. Cl. ................................................................ 424/423
[58] Field of Search ....................................................... 424/423

[56] References Cited

U.S. PATENT DOCUMENTS

| | | | |
|---|---|---|---|
| 3,914,412 | 10/1975 | Gendrich et al. | 424/177 |
| 4,547,370 | 10/1985 | Roeske | 514/15 |
| 4,661,472 | 4/1987 | Rivier et al. | 514/15 |
| 4,689,396 | 8/1987 | Roeske et al. | 530/313 |
| 4,851,385 | 7/1989 | Roeske | 514/15 |
| 5,034,229 | 7/1991 | Magruder et al. | 424/422 |
| 5,057,318 | 10/1991 | Magruder et al. | 424/438 |
| 5,110,596 | 5/1992 | Magruder et al. | 424/438 |
| 5,198,533 | 3/1993 | Schally et al. | 530/313 |
| 5,413,990 | 5/1995 | Haviv et al. | 514/15 |
| 5,480,868 | 1/1996 | Kamei et al. | 514/15 |
| 5,482,931 | 1/1996 | Harris et al. | 514/15 |
| 5,498,598 | 3/1996 | Harris | 514/11 |

FOREIGN PATENT DOCUMENTS

| | | |
|---|---|---|
| 0111841 | 6/1984 | European Pat. Off. |
| WO92/20711 | 11/1992 | WIPO . |
| WO94/19020 | 9/1994 | WIPO . |
| WO95/00168 | 1/1995 | WIPO . |
| WO95/01183 | 1/1995 | WIPO . |
| WO95/04540 | 2/1995 | WIPO . |
| WO96/07398 | 3/1996 | WIPO . |
| WO97/27840 | 8/1997 | WIPO . |

OTHER PUBLICATIONS

Fu Lu, et al., "Percutaneous Absorption Enhancement of Leuprolide", *Pharm. Res.*, 9(12):1575–1576 (1992).
Helm, et al., "Stability of Gonadorelin and Triptorelin in Aqueous Solution", *Pharm. Res.*, 7(12):1253–1256 (1990).
Johnson, et al., "Degradation of the LH–RH Analog Nafarelin Acetate in Aqueous Solution", *Intl. J. Pharm.*, 31:125–129 (1986).

(List continued on next page.)

*Primary Examiner*—Carlos A Azpuru
*Attorney, Agent, or Firm*—Mary Ann Dillahunty; Steven F. Stone; Pauline A. Clarke

[57] ABSTRACT

This invention relates to stable liquid aqueous formulations of peptide compounds at high concentrations. These stable formulations comprise at least about 10% peptide in water. They may be stored at elevated temperatures for long periods of time and are especially useful in implantable delivery devices for long term delivery of drug.

30 Claims, 5 Drawing Sheets

OTHER PUBLICATIONS

Okada, et al., "Preparation of Three–Month Depot Injectable Microspheres of Leuprorelin Acetate Using Biodegradable Polymers", *Pharm. Res.*, 11(8):1143–1147 (1994).

Okada, et al., "New Degradation Product of Des–Gly$^{10}$–NH$_2$–LH–RH–Ethylamide (Fertirelin) in Aqueous Solution", *J. Pharm. Sci.*, 80(2):167–170 (1991).

Oyler, et al., "Characterization of the Solution Degradation Products of Histrelin, a Gonadotropin Releasing Hormone (LH/RH) Agonist", *J. Pharm. Sci.*, 80(3):271–275 (1991).

Powell, et al., "Peptide Liquid Crystals: Inverse Correlation of Kinetic Formation and Thermodynamic Stability in Aqueous Solution", *Pharm. Res.*, 11(9):1352–1354 (1994).

Powell, et al., "Parenteral Peptide Formulations: Chemical and Physical Properties of Native Luteinizing Hormone–Releasing Hormone (LHRH) and Hydrophobic Analogues in Aqueous Solution", *Pharm. Res.*, 8(10):1258–1263 (1991).

Powers, et al., "Solution Behavior of Leuprolide Acetate, an LHRH Agonist, as Determined by Circular Dichroism Spectroscopy", *Intl. J. Pharm.,* 108:49–55 (1994).

Shi, et al., "Long–Term Stability of Aqueous Solutions of Luteinizing Hormone–Releasing Hormone Assessed by an In–Vitro Bioassay and Liquid Chromatography", *J. Pharm. Sci.*, 73(6):819–821 (1984).

Toguchi, "Pharmaceutical Manipulation of Leuprorelin Acetate to Improve Clinical Performance", *J. Intl. Med. Res.*, 18:35–41 (1990).

Factrel (gonadorelin HCl for subcutaneous or IV injection), Physician's Desk Reference, 50th Edition, pp. 2877–2878 (1996).

Lupron (leuprolide acetate for subcutaneous injection), Physician's Desk Reference, 50th Edition, pp. 2555–2556 (1996).

Lupron Depot (leuprolide acetate for depot suspension), Physician's Desk Reference, 50th Edition, pp. 2556–2562 (1996).

Lutrepulse (gonadorelin acetate for IV injection), Physician's Desk Reference, 50th Edition, pp. 980–982 (1996).

Zoladex (goserelin acetate implant), Physician's Desk Reference, 50th Edition, pp. 2858–2861 (1996).

AQUEOUS FORMULATIONS OF PEPTIDES

CROSS-REFERENCE TO RELATED APPLICATIONS

This application is a continuation of application Ser. No. 08/874,694, filed Jun. 13, 1997, now U.S. Pat. No. 5,916,582, which is a continuation-in-part of application No. 60/021,199 filed Jul. 3, 1996.

FIELD OF THE INVENTION

This invention relates to stable aqueous formulations of peptide compounds at high concentrations.

BACKGROUND OF THE INVENTION

References

The following references are referred to by numbers in brackets ([ ]) at the relevant portion of the specification.
1. Zoladex (goserelin acetate implant), Physician's Desk Reference, 50th Edition, pages 2858–2861 (1996).
2. U.S. Pat. No. 3,914,412, issued Oct. 21, 1975.
3. U.S. Pat. No. 4,547,370, issued Oct. 15, 1985.
4. U.S. Pat. No. 4,661,472, issued Apr. 28, 1987.
5. U.S. Pat. No. 4,689,396, issued Aug. 25, 1987.
6. U.S. Pat. No. 4,851,385, issued Jul. 25, 1989.
7. U.S. Pat. No. 5,198,533, issued Mar. 30, 1993.
8. U.S. Pat. No. 5,480,868, issued Jan. 2, 1996.
9. WO92/20711, published Nov. 26, 1992.
10. WO95/00168, published Jan. 5, 1995.
11. WO95/04540, published Feb. 16, 1995.
12. "Stability of Gonadorelin and Triptorelin in Aqueous Solution", V. J. Helm, B. W. Muller, *Pharmaceutical Research*, 7/12, pages 1253–1256 (1990).
13. "New Degradation Product of Des-Gly$^{10}$—NH$_2$—LHRH-Ethylamide (Fertirelin) in Aqueous Solution", J. Okada, T. Seo, F. Kasahara, K. Takeda, S. Kondo, *J. of Pharmaceutical Sciences*, 8012, pages 167–170 (1991).
14. "Characterization of the Solution Degradation Product of Histrelin, a Gonadotropin Releasing Hormone (LHRH) Agonist", A. R. Oyler, R. E. Naldi, J. R. Lloyd, D. A. Graden, C. J. Shaw, M. L. Cotter, *J. of Pharmaceutical Sciences*, 80/3, pages 271–275 (1991).
15. "Parenteral Peptide Formulations: Chemical and Physical Properties of Native Luteinizing Hormone-Releasing Hormone (LHRH) and Hydrophobic Analogues in Aqueous Solution", M. F. Powell, L. M. Sanders, A. Rogerson, V. Si, *Pharmaceutical Research*, 8/10, pages 1258–1263 (1991).
16. "Degradation of the LHRH Analog Nafarelin Acetate in Aqueous Solution", D. M. Johnson, R. A. Pritchard, W. F. Taylor, D. Conley, G. Zuniga, K. G. McGreevy, *Intl. J. of Pharmaceutics*, 31, pages 125–129 (1986).
17. "Percutaneous Absorption Enhancement of Leuprolide", M. Y. Fu Lu, D. Lee, G. S. Rao, *Pharmaceutical Research*, 9/12, pages 1575–1576 (1992).
18. Lutrepulse (gonadorelin acetate for IV injection), Physician's Desk Reference, 50th Edition, pages 980–982 (1996).
19. Factrel (gonadorelin HCl for subcutaneous or IV injection), Physician's Desk Reference, 50th Edition, pages 2877–2878 (1996).
20. Lupron (leuprolide acetate for subcutaneous injection), Physician's Desk Reference, 50th Edition, pages 2555–2556 (1996).
21. Lupron depot (leuprolide acetate for depot suspension), Physician's Desk Reference, 50th Edition, pages 2556–2562 (1996).
22. "Pharmaceutical Manipulation of Leuprorelin Acetate to Improve Clinical Performance", H. Toguchi, *J. of Intl. Medical Research*, 18, pages 35–41 (1990).
23. "Long-Term Stability of Aqueous Solutions of Luteinizing Hormone-Releasing Hormone Assessed by an In-Vitro Bioassay and Liquid Chromatography", Y. F. Shi, R. J. Sherins, D. Brightwell, J. F. Gallelli, D. C. Chatterji, *J. of Pharmaceutical Sciences*, 73/6, pages 819–821 (1984).
24. "Peptide Liquid Crystals: Inverse Correlation of Kinetic Formation and Thermodynamic Stability in Aqueous Solution", M. F. Powell, J. Fleitman, L. M. Sanders, V. C. Si, *Pharmaceutical Research*, 11/9, pages 1352–1354 (1994).
25. "Solution Behavior of Leuprolide Acetate, an LHRH Agonist, as Determined by Circular Dichroism Spectroscopy", M. E. Powers, A. Adejei, M. Y. Fu Lu, M. C. Manning, *Intl. J. of Pharmaceutics*, 108, pages 49–55 (1994).
26. "Preparation of Three-Month Depot Injectable Microspheres of Leuprorelin Acetate Using Biodegradable Polymers", *Pharmaceutical Research*, 1118, pages 1143–1147 (1994).

The disclosure of each of the above publications, patents or patent applications is hereby incorporated by reference in its entirety to the same extent as if the language of each individual publication, patent and patent application were specifically and individually incorporated by reference.

Luteinizing hormone-releasing hormone (LHRH), also known as gonadotropin releasing hormone (GnRH), is a decapeptide with the structure:

pGlu-His-Trp-Ser-Tyr-Gly-Leu-Arg-Pro-Gly-NH$_2$.

It is secreted by the hypothalamus and binds to receptors on the pituitary gland, releasing luteinizing hormone (LH) and follicle stimulating hormone (FSH). LH and FSH stimulate the gonads to synthesize steroid hormones. Numerous analogs of LHRH are known, including peptides related to LHRH which act as agonists and those which act as antagonists. [1–15] LHRH analogs are known to be useful for treating hormone-dependent diseases such as prostate cancer, benign prostatomegaly, endometriosis, hysteromyoma, metrofibroma, precocious puberty, or mammary cancer and as contraceptives. [8] Sustained release administration is preferred for both agonist LHRH-related compounds, which reduce the number of available receptors after repeated administration so that the production of steroid hormones is suppressed, and antagonist LHRH-related compounds, which must be continually administered for persistent inhibition of endogenous LHRH. [8]

The sustained parenteral delivery of drugs, especially peptide drugs, provides many advantages. The use of implantable devices for sustained delivery of a wide variety of drugs or other beneficial agents is well known in the art. Typical devices are described, for example, in U.S. Pat. Nos. 5,034,229; 5,057,318; and 5,110,596. The disclosure of each of these patents is incorporated herein by reference.

In general, oral bioavailability of peptides, including LHRH-related compounds, is low. [16–17]

Currently marketed aqueous formulations of LHRH, its analogs and related compounds which are used for parenteral injection generally contain relatively low concentrations of LHRH-related compounds (0.05 to 5 mg/ml) and may also contain excipients such as mannitol or lactose. [18–20] Such formulations of LHRH-related compounds must either be stored refrigerated or may be stored at room temperature for short periods of time.

Available depot formulations of LHRH-related compounds administered for sustained release over a period of 1–3 months include a formulation comprised of 15% LHRH-related compound dispersed in a matrix of D,L-lactic and glycolic acids copolymer presented as a cylinder to be injected subcutaneously [1] and a formulation comprised of microparticles comprising a core of LHRH-related compound and gelatin surrounded by a shell of D,L-lactic and glycolic acids copolymer. These microparticles are suspended in a diluent for injection either subcutaneously or intramuscularly. [21, 26] These products must be stored at room temperature or lower. Aqueous formulations of LHRH-related compounds are known to exhibit both chemical and physical instability, as well as degradation after irradiation. [12–16, 22–25]

Formulations which have been shown to be stable ($t_{90}$ about five years) have been very low concentration (25 μg/ml) aqueous, buffered (10 mM buffer, ionic strength of 0.15) solutions stored at temperatures no higher than room temperature (25° C.). [15]

There is a need for stable, high concentration aqueous formulations of peptides.

SUMMARY OF THE INVENTION

The present invention provides stable aqueous formulations which are solutions of peptides compounds in water at concentrations of at least about 10%. These stable high concentration formulations may be stored at elevated temperatures (e.g., 37° C.) for long periods of time and are especially useful in implantable delivery devices for long term delivery (e.g., 1–12 months or longer) of drug. The aqueous formulations may optionally include buffer, excipients, ethanol (EtOH), a surfactant or a preservative.

In one aspect, the invention provides stable aqueous formulations of peptide compounds, said formulations comprising at least about 10% (w/w) peptide compound and water.

In another aspect, the invention provides methods for preparing a stable aqueous formulation of an peptide compound, said methods comprising dissolving at least about 10% (w/w) peptide compound in water.

In yet a further aspect, the invention provides methods for treating a subject suffering from a condition which may be alleviated by administration of a peptide compound, said methods comprising administering to said subject an effective amount of a stable aqueous formulation comprising at least about 10% (w/w) peptide compound and water.

DETAILED DESCRIPTION OF THE INVENTION

The present invention is drawn to the unexpected discovery that dissolving high concentrations (i.e., at least about 10%) of peptide compounds in water results in stable aqueous formulations. Previously known aqueous formulations of peptide compounds, which are dilute buffered aqueous solutions containing excipients such as EDTA or ascorbic acid which must be stored at low temperatures (4–25° C.), form degradation products using degradation pathways such as acid/base catalyzed hydrolysis, deamidation, racemization and oxidation. In contrast, the presently claimed formulations stabilize peptide compounds at high concentrations at elevated temperatures (e.g., 37° C. to 80° C.), thus making possible the delivery of peptides in implantable delivery devices that would not otherwise be feasible.

Standard peptide and protein formulations consist of dilute aqueous solutions. Two critical aspects of peptide formulation include solubilization and stabilization of the drug molecule. Peptide stability is usually achieved by varying one or more of the following: pH, buffer type, ionic strength, excipients (EDTA, ascorbic acid, etc.). In contrast, in the present invention, highly concentrated peptides formulated in water provide stable solutions.

The invention consists of using high concentrations of peptide in aqueous solution to stabilize the peptide formulations against both chemical and physical degradation.

A. Definitions

As used herein, the following terms have the following meanings:

The term "chemical stability" means that an acceptable percentage of degradation products produced by chemical pathways such as oxidation or hydrolysis is formed. In particular, a formulation is considered chemically stable if no more than about 20% breakdown products are formed after two months at 37° C.

The term "physical stability" means that an acceptable percentage of aggregates (e.g., dimers, trimers and larger forms) is formed. In particular, a formulation is considered physically stable if no more that about 15% aggregates are formed after two months at 37° C.

The term "stable formulation" means that at least about 65% chemically and physically stable peptide compound remains after two months at 37° C. (or equivalent conditions at an elevated temperature). Particularly preferred formulations are those which retain at least about 80% chemically and physically stable peptide under these conditions. Especially preferred stable formulations are those which do not exhibit degradation after sterilizing irradiation (e.g., gamma, beta or electron beam).

The terms "peptide" and/or "peptide compound" mean polymers of up to about 50 amino acid residues bound together by amide (CONH) linkages. Analogs, derivatives, agonists, antagonists and pharmaceutically acceptable salts of any of these are included in these terms. The terms also include peptides and/or peptide compounds which have D-amino acids, modified, derivatized or non-naturally occurring amino acids in their D- or L-configuration and/or peptomimetic units as part of their structure.

The term "LHRH-related compound" means luteinizing hormone releasing hormone (LHRH) and its analogs and pharmaceutically acceptable salts. Octa-, nona- and decapeptide LHRH agonists and antagonists are included in the term LHRH-related compounds, as is native LHRH. Particularly preferred LHRH-related compounds include LHRH, leuprolide, goserelin, nafarelin, and other known active agonists and antagonists. [1–21]

The term "high concentration" means at least about 10% (w/w) and up to the maximum solubility of the particular LHRH-related compound.

The term "excipient" means a more or less inert substance in a formulation which is added as a diluent or vehicle or to give form or consistency. Excipients are distinguished from solvents such as EtOH, which are used to dissolve drugs in formulations, from non-ionic surfactants such as Tween 20, which are used to solubilize drugs in formulations, and from preservatives such as benzyl alcohols or methyl or propyl parabens, which are used to prevent or inhibit microbial growth.

The term "buffering capacity" means the capacity of a solution due to the presence of a mixture of an acid/base pair in the solution to reduce any changes in pH that would otherwise occur in the solution when acid or alkali is added to it.

The term "polar aprotic solvent" means a polar solvent which does not contain acidic hydrogen and does not act as a hydrogen bond donor. Examples of polar aprotic solvents are dimethylsulfoxide (DMSO), dimethylformamide (DMF), hexamethylphosphorotriamide (HMPT), and n-methyl pyrrolidone.

B. Preparation of Formulations

The present invention is drawn to highly concentrated liquid aqueous formulations of peptide compounds which are stable for prolonged periods of time at elevated temperatures. Standard dilute aqueous peptide and protein formulations require manipulation of buffer type, ionic strength, pH and excipients (e.g., EDTA and ascorbic acid) to achieve stability. In contrast, the claimed formulations achieve stabilization of peptide compounds by the use of high concentrations (at least about 10%, w/w) of compound dissolved in water.

Examples of peptides and peptide compounds which may be formulated using the present invention include those peptides which have biological activity or which may be used to treat a disease or other pathological condition. They include, but are not limited to adrenocorticotropic hormone, angiotensin I and II, atrial natriuretic peptide, bombesin, bradykinin, calcitonin, cerebellin, dynorphin A, alpha and beta endorphin, endothelin, enkephalin, epidermal growth factor, fertirelin, follicular gonadotropin releasing peptide, galanin, glucagon, gonadorelin, gonadotropin, goserelin, growth hormone releasing peptide, histrelin, insulin, leuprolide, LHRH, motilin, nafarelin, neurotensin, oxytocin, somatostatin, substance P, tumor necrosis factor, triptorelin, and vasopressin. Analogs, derivatives, antagonists, agonists and pharmaceutically acceptable salts of the above may also be used.

Depending on the particular peptide compound to be formulated, ionic strength and pH may be factors worthy of consideration. For example, we have found that preferred aqueous formulations of leuprolide acetate have low ionic strength and pH between about 4 and about 6.

The peptide compounds useful in the formulations and methods of the present invention can be used in the form of a salt, preferably a pharmaceutically acceptable salt. Useful salts are known to those of skill in the art and include salts with inorganic acids, organic acids, inorganic bases or organic bases. Preferred salts are acetate salts.

Peptide compounds which are hydrophilic and readily soluble in water are preferred for use in the present invention. One of skill in the art can easily determine which compounds will be useful on the basis of their aqueous solubility, i.e., the compound must be soluble in water to at least about 10% (w/w). Preferably, this is also a pharmaceutically effective amount. Particularly preferred peptide compounds are LHRH-related compounds, including leuprolide and leuprolide acetate.

The proportion of peptide may vary depending on the compound, the condition to be treated, the solubility of the compound, the expected dose and the duration of administration. (See, for example, *The Pharmacological Basis of Therapeutics*, Gilman et al., 7th ed. (1985) and *Pharmaceutical Sciences*, Remington, 18th ed. (1990), the disclosures of which are incorporated herein by reference.) The concentration of peptide compound may range from at least about 10% (w/w) to the maximum solubility of the compound. A preferred range is from about 20 to about 60% (w/w). The currently more preferred range is from about 30 to about 50% (w/w) and a most preferred range is about 35 to about 45% (w/w).

Generally, the stable formulations of the present invention may be prepared by simply dissolving a therapeutically effective amount of the desired peptide compound in water, although pH adjustments may be made.

It is known to those of skill in the art that buffers, excipients, solvents such as EtOH, solubilizers such as non-ionic surfactants, and preservatives may beneficially be added to pharmaceutical peptide formulations. (See, for example, *Pharmaceutical Sciences*, Remington, 18th ed. (1990).) Such agents may optionally be added to the claimed formulations.

C. Methodology

We have found that stable aqueous formulations of peptide compounds may be prepared by dissolving a high concentration (at least about 10%) of the peptide compound to be formulated in water.

Figure 1:
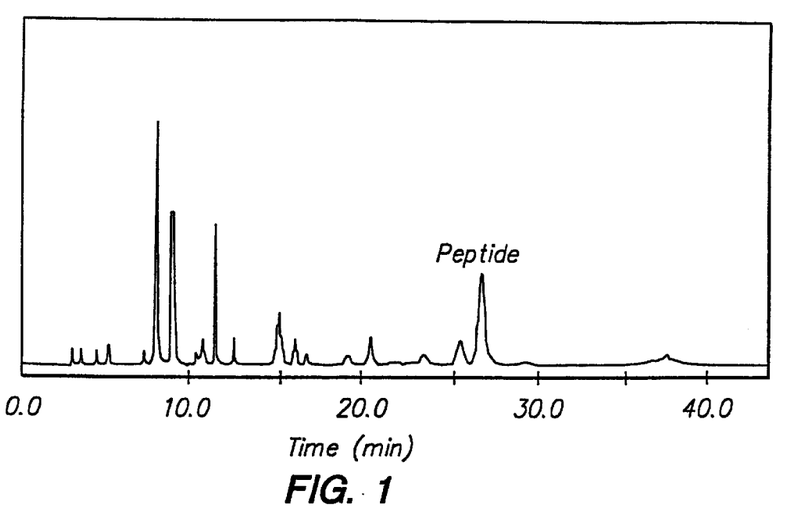
FIG. 1 illustrates the stability of 40% leuprolide acetate solution in water after two months at 80° C. as measured by reverse phase HPLC (RP-HPLC).
Figure 6:
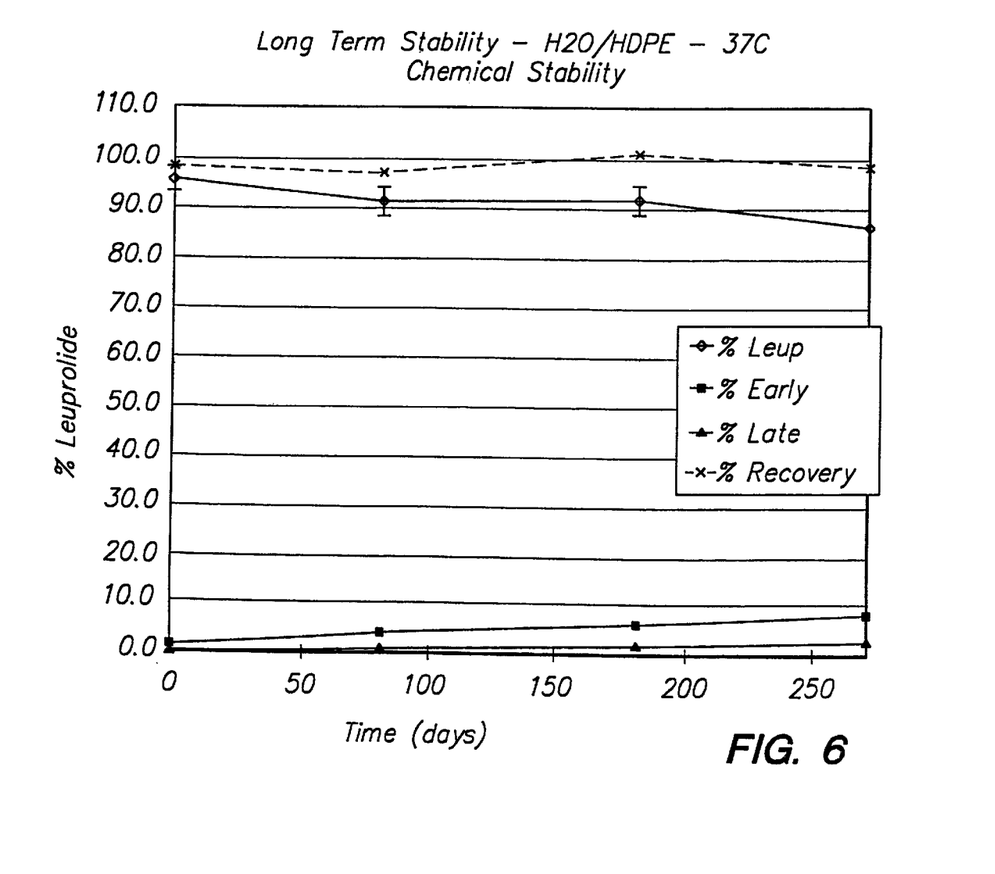
FIG. 6 illustrates the chemical and physical stability of a 40% leuprolide acetate solution in water after nine months at 37° C.

We have tested these peptide compound formulations, specifically formulations of the LHRH-related compound leuprolide, for stability by subjecting them to accelerated aging at elevated temperature and measuring the chemical and physical stability of the formulations. Results of these studies (shown, for example, in Table III and FIGS. 1, 2 and 6) demonstrate that these formulations were stable at conditions that approximate or exceed storage for one year at 37° C.

We have also tested peptide compound formulations prepared as described herein for stability after 2.5 megarad gamma irradiation. Results, shown in Table IV, show that these formulations remained chemically and physically stable after such irradiation. Formulations subjected to electron beam irradiation were also found to be stable.

As shown in Table I, we have tested a wide variety of peptide formulations, specifically leuprolide, goserelin, LHRH, angiotensin I, bradykinin, calcitonin, insulin, trypsinogen and vasopressin, for stability by dissolving (or attempting to dissolve) them in water, then subjecting them to accelerated aging at elevated temperatures. The stability of the formulations was measured. Results are presented in Table I as half-life at 37° C. assuming an $E_a$=22.2 kcal/mole. A wide range of the peptides tested were soluble in water and remained stable under the test conditions. The solubility of a particular peptide in water and the stability of the resulting solution are easily determined using routine procedures known to those of ordinary skill in the art.

TABLE I

Stability of Peptides Formulated in Water

| FORMULATION | HALF-LIFE* (Temperature) |
|---|---|
| 40% Leuprolide | 9.7 years (37° C.) |
| 40% Goserelin | 19.3 months (80° C.) |
| 20% LHRH | 2.5 years (65° C.) |
| 20% Angiotensin I | insoluble gel (65° C.) |
| 20% Bradykinin | 8.5 months (65° C.) |
| 40% Calcitonin | insoluble (80° C.) |
| 20% Calcitonin | 9.6 months (80° C.) |
| 5% Calcitonin | 23.5 months (50° C.) |
| 20% Insulin | insoluble gel (65° C.) |
| 40% Trypsinogen | insoluble gel (65° C./80° C.) |
| 20% Trypsinogen | insoluble gel (65° C.) |
| 40% Vasopressin | degraded (80° C.) |
| 20% Vasopressin | 14.3 days (65° C.) |

*Half-life at 37° C. assuming $E_a$ = 22.2 kcal/mole.

Formulations of 40% leuprolide in water stored for six months at 37° C. showed linear degradation as measured by overall loss of peptide from the solution. Analysis of these data gave an activation energy ($E_a$) of 22.2 kcal/mole and a $t_{90}$ of 13.8 months, showing stability of these formulations at elevated temperatures.

We have also unexpectedly found that certain peptide formulations of the present invention are bacteriostatic (i.e., inhibit bacterial growth), bactericidal (i.e., cause the death of bacteria), and sporicidal (i.e., kill spores). In particular, leuprolide formulations of 50–400 mg/ml exhibited bacteriostatic, bactericidal and sporicidal activity. The stability of the samples was unaffected by spiking with bacteria, indicating that the enzymes released from the killed and lysed bacteria did not adversely affect the stability of the product. This demonstrates that these formulations were not conducive to enzymatic activity.

Some peptides, for example calcitonin and leuprolide, are known to be physically unstable, exhibiting aggregation, gelation and fibrillation when formulated in aqueous solution. For example, leuprolide can be induced to gel by increasing peptide concentration, introduction of salts or gentle agitation. Improving physical stability can allow for easier parenteral administration, including administration using implantable drug delivery systems.

It has unexpectedly been found that adding polar aprotic solvents such as DMSO to aqueous formulations of certain peptides, such as leuprolide, goserelin and calcitonin, prevents gelation of the formulation. This is apparently because non-aqueous polar aprotic solvents cause peptides to form a random coil/alpha helix conformation that does not refold into a beta sheet structure and, therefore, does not gel. Thus, these solvents have an anti-gellant effect.

Figure 8:
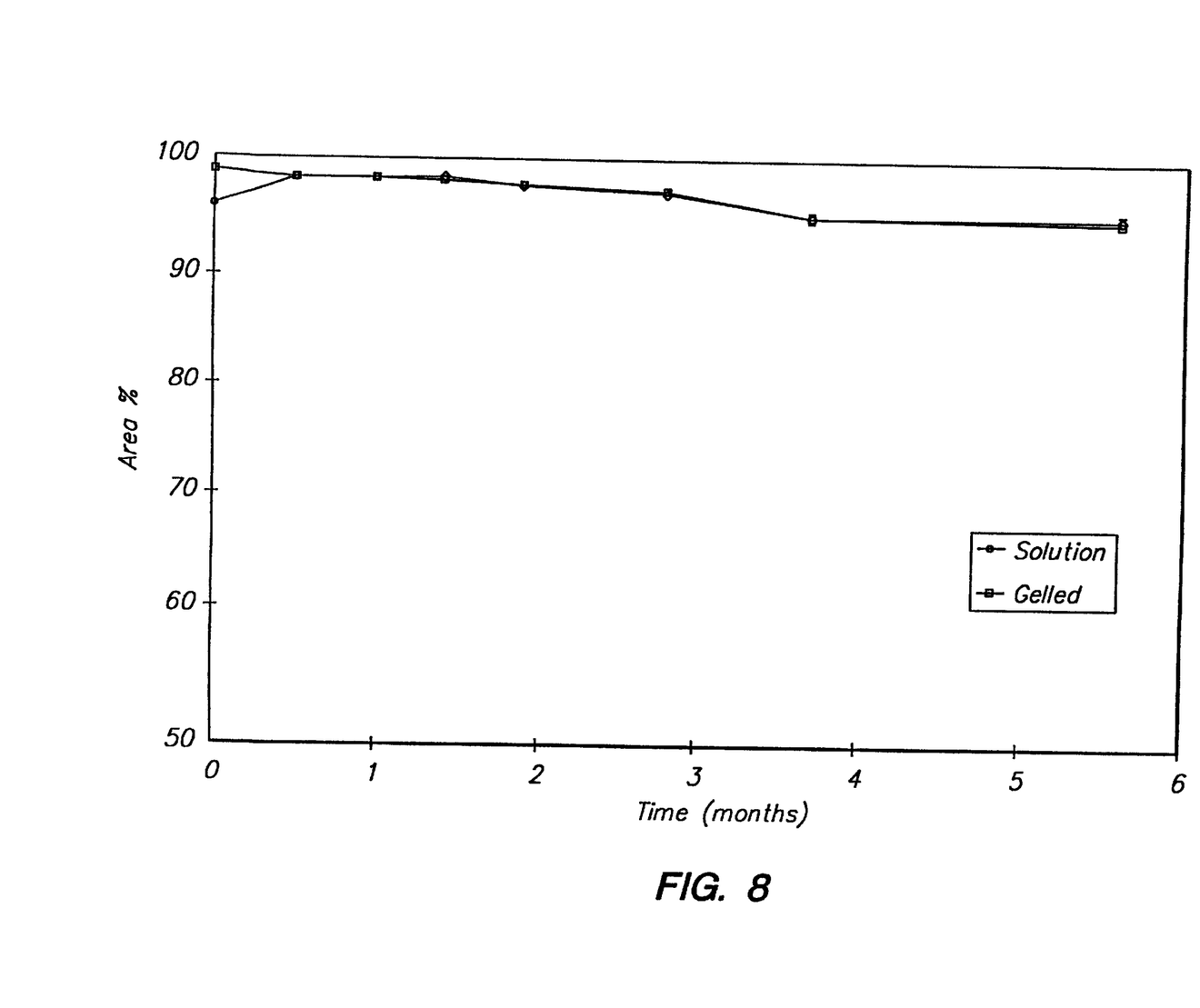
FIG. 8 illustrates that both gelled and non-gelled aqueous formulations of leuprolide (370 mg/ml) remained stable over a period of 6 months at 37° C.

Additionally, studies of gelled and non-gelled aqueous formulations of leuprolide (370 mg/ml) stored at 37° C. for 6 weeks showed a similar chemical stability profile as assayed by RP-HPLC. Results are shown in FIG. 8. Similarly, the stability of liquid and gelled (by agitation) aqueous leuprolide formulations (370 mg/ml) was studied in vitro at 37° C. and in vivo in rats, respectively. Results are presented in Table II, and show that the both gelled and liquid formulations remained stable over a period of 18 weeks.

TABLE II

Stability Studies of Liquid and Gelled Aqueous Leuprolide Formulations

| STUDY | TIME (weeks) | LIQUID (% remaining) | GELLED (% remaining) |
|---|---|---|---|
| Long Term Stab | 6 | 98.00 | |
| Long Term Stab | 12 | 91.50 | |
| Long Term Stab | 18 | 93.50 | |
| Rat | 4 | | 94.80 |
| Rat | 6 | | 93.50 |
| Rat | 12 | | 92.30 |
| Rat | 18 | | 92.60 |

A major aspect of the invention is that aqueous solutions containing high concentrations of peptide compounds are stable at high temperatures for long periods of time. Thus, these formulations are advantageous in that they may be shipped and/or stored for long periods of time at or above room temperature. They are also suitable for use in implantable delivery devices.

DISCLOSURE OF EXAMPLES OF THE INVENTION

The following methods were used to perform the studies in the Examples that follow.

1. Preparing Leuprolide Acetate Solutions

Leuprolide acetate (obtained, for example, from Mallinckrodt, St. Louis, Mo.) was weighed, added to a weighed amount of vehicle (sterile distilled water, ethanol/water or water with non-ionic surfactant) at the appropriate concentration (w/w), then gently stirred to dissolve.

Unless otherwise noted, leuprolide free base content was calculated from certificate of analysis potency values to be 37% free base. This was 40% leuprolide acetate, except as noted.

2. Preparation of Reservoirs

The reservoirs of implantable drug delivery devices (as disclosed in U.S. patent application Ser. No. 08/595,761, incorporated herein by reference) were filled with the appropriate leuprolide acetate solution. The filled devices then underwent stability testing. The formulation was filled into titanium or polymer reservoirs with a polymer plug blocking each end. The filled reservoir was then sealed in a polyfoil bag and placed in a stability testing oven.

It should be noted that the formulations in the reservoirs of these devices are completely isolated from the outside environment.

3. Reverse Phase-HPLC (RP-HPLC)

All stability samples were analyzed for leuprolide concentration and % peak area using a gradient elution reversed-phase HPLC assay with a refrigerated autosampler (4° C.) to minimize sample degradation. The chromatographic conditions used are listed below.

| RP-HPLC Chromatographic Conditions | |
| --- | --- |
| Description | Parameter |
| Column | HaiSil C18, 4.6 × 250 mm, S/N 5103051 |
| Flow Rate | 0.8 mL min$^{-1}$ |
| Injection Volume | 20 μL |
| Detection | 210 nm |
| Leuprolide Retention Time | Between 25–30 minutes |
| Mobile Phase | A = 100 mM Sodium Phosphate, pH 3.0<br>B = 90% Acetonitrile/Water |
| Gradient | Minutes 0  5    25   40  41  46  46.1  50<br>%B         15 26.5 26.5 65  85  85   15  15 |

Leuprolide standards (in water) at 4 to 6 different concentration levels, typically between 0.1–1.2 mg/mL, were run along with the stability samples. The stability samples were bracketed by the standard sets, with no more than 40 samples in between the standard sets. All peaks between the void volume and 45 minutes of the run were integrated. The integrated peak areas for the leuprolide standards were plotted as a function of the concentration. The leuprolide concentrations for the stability samples were then calculated using linear regression. The % peak areas for the leuprolide peak, the sum of all the peaks eluting before leuprolide (labeled "others"), and the sum of all the peaks eluting after leuprolide (labeled "aggregates") were also recorded and plotted as a function of the sample timepoints.

4. Size Exclusion Chromatography (SEC)

Selected stability samples were analyzed for % peak area and molecular weights using an isocratic solution SEC assay with a refrigerated autosampler (4° C.). The chromatographic conditions used are listed below.

| SEC Chromatographic Conditions | |
| --- | --- |
| Description | Parameter |
| Column | Pharmacia Peptide, HR 10/30, 10 × 300 mm |
| Flow Rate | 0.5 mL min$^{-1}$ |
| Injection Volume | 20 μL |
| Detection | 210 nm |
| Leuprolide Retention Time | Approximately 25 minutes |
| Mobile Phase | 100 mM Ammonium Phosphate, pH 2.0, 200 mM Sodium Chloride, 30% Acetonitrile |

The void volume and total volume for the size exclusion column was needed for the calculation of the molecular weights. The BioRad high molecular weight standard and 0.1% acetone were used to determine the void volume and total volume respectively. The retention times for the first peak in the BioRad standard and the acetone peak were recorded and converted to volume units using the equations below. Since these values are constant for a particular SEC column and HPLC system, the void and total volumes were redetermined whenever changes to the SEC column or HPLC system were made. A standard run was then made followed by the stability samples. The standard mixture contained approximately 0.2 mg/mL of the following peptides: Bursin (MW=449), WLFR peptide (MW=619), Angiotensin (MW=1181), GRF (MW=5108), and Cytochrome C (MW=12394). These standards were chosen because they bracketed leuprolide molecular weight and all had basic pI (9.8–11.0), similar to leuprolide.

The % peak areas were recorded for all the peaks. The molecular weights for the species separated were calculated using the equations below.

$V_s$=flow rate (mL/min)×sample peak retention time (min)

$V_o$=flow rate (mL/min)×void volume peak retention time (min)

$V_t$=flow rate (mL/min)×total volume peak retention time (min)

$$Kd = \frac{V_s - V_o}{V_t - V_o}$$

Where:

$V_s$=standard or sample volume $V_o$=void volume $V_t$=total volume $V_s$ was calculated to each peptide standard peak. Kd for each peptide standard was then calculated using the values for $V_t$ and $V_o$ determined earlier. The linear regression line from the plot of logMW vs. Kd$^{-1}$ was used to determine the molecular weights for each peak in the stability sample. The % peak areas for the stability samples were also recorded.

5. Instrumentation and Materials

The instrumentation and materials used for RP-HPLC and SEC were as follows:

Waters Millennium HPLC system consisting of 717 autosampler, 626 pump, 6000S controller, 900 photodiode array detector, and 414 refractive index detector (Waters Chromatography, Milford, Mass.)

HPLC vials, for 48-position and 96-position (Waters Chromatography, Milford, Mass.)

HaiSil C18, 120 A, 5 μm4.6×250 mm HPLC column (Higgins Analytical, Mountain View, Calif.)

Pharmacia Peptide, HR 10/30 SEC column (Pharmacia Biotech, Piscataway, N.J.)

6. Purity

Stability samples were analyzed using RP-HPLC. The area under the curve for the leuprolide peak divided by the sum of the areas under the curve of all peaks gave % purity. [It should be noted that the data for % concentration presented with the % purity data (Examples 5, 6 and 7) are inconclusive. The analysis methods used to determine % concentration in these experiments were unreliable.]

The following examples are offered to illustrate this invention and are not meant to be construed in any way as limiting the scope of this invention.

EXAMPLE 1

Accelerated Stability Studies of Leuprolide Acetate Formulations

Formulations of 40% (w/w) leuprolide acetate (equivalent to about 37% leuprolide free base) in either sterile distilled water, ethanol/water (70/30) or water with 10% Tween 20 were prepared as described above and used to fill the reservoirs of implantable drug delivery devices, also as described above. Some reservoirs were made of polymer materials, while some were titanium.

The filled devices were subjected to accelerated aging by storing them at elevated temperatures (80–88° C.) for seven days in an incubator (Precision Scientific or Thelco). This is equivalent to about 1.5 years at 37° C. or about four years at room temperature (25° C.), assuming an activation energy ($E_a$) or 22.2 kcal/mole.

The samples were analyzed using RP-HPLC and SEC as described above to determine the chemical and physical stability of the aged formulations.

Results, presented in Table III, demonstrate that these aqueous formulations were able to maintain the stability of the LHRH-related compound leuprolide. In each case, at least 65% leuprolide was retained. However, a large amount of the formulation with EtOH evaporated from the reservoir during the study, indicating that long term storage at elevated temperatures of formulations with high concentrations of a volatile solvent like EtOH may be problematic. The formulation which contained the non-ionic surfactant 10% Tween 20 was found to be no more stable that water solutions without this solubilizer.

TABLE III

Stability of 40% (w/w) Leuprolide Acetate Aqueous Formulations After 7 Days at Elevated Temperatures

| Temperature (° C.) | Reservoir Material | Formulation | % Leuprolide at Day 7 |
|---|---|---|---|
| 88 | Polymer | 40% in Water | 68 |
| 88 | Titanium | 40% in Water | 71 |
| 88 | Polymer | 40% in Water | 66* |
| 88 | Polymer | 40% in EtOH/H$_2$O (07/30) | 85** |
| 88 | Polymer | 40% in 10% Tween 20 | 65 |
| 80 | Polymer | 40% in Water | 83 |
| 80 | Polymer | 40% in Water | 80 |
| 80 | Polymer | 40% in Water | 78 |
| 80 | Polymer | 40% in Water | 79 |
| 80 | Polymer | 40% in Water | 83 |
| 80 | Polymer | 40% in Water | 77 |
| 80 | Polymer | 40% in Water | 79 |
| 80 | Polymer | 40% in Water | 74 |
| 80 | Polymer | 40% in Water | 88 |

*10% evaporated
**60% evaporated

EXAMPLE 2

Stability Studies of Irradiated Leuprolide Acetate Formulations

Formulations of 40% (w/w) as received leuprolide acetate (equivalent to 37% leuprolide free base) in water were prepared as described above and used to fill the reservoirs of drug delivery devices, also as described above. Some reservoirs were made of polymer materials, while some were titanium.

The filled devices were subjected to 2.5 megarad gamma irradiation. Samples were shipped to Sterigenics (Tustin, Calif.) and gamma irradiated (Cobalt 60) in batch mode. Samples were then subjected to accelerated aging as in Example 1. Samples labeled "cold" were shipped and irradiated on dry ice. Samples were taken at day 0 and day 7, and analyzed using RP-HPLC and SEC as described above to determine the chemical and physical stability of the irradiated formulations.

Results, presented in Table IV, demonstrate that these leuprolide acetate formulations were stable after irradiation. In every case, at least 65% leuprolide was retained, with low levels of aggregate formation.

TABLE IV

Stability of 40% (w/w) Leuprolide Acetate Aqueous Formulations After 2.5 Megarad Gamma Irradiation

| Reservoir Material | Formulation | Irradiation | % Leuprolide at Day 7 (RP-HPLC) | SEC Day 0 | | SEC Day 7 | |
|---|---|---|---|---|---|---|---|
| | | | | % monomer | % dimer/trimer | % monomer | % dimer/trimer |
| Polymer | 40% in Water | Yes | 75 | 90.4 | 1.2 | 80.9 | 3.9 |
| Polymer | 40% in Water | No | 75 | 99.8 | 0.2 | 82.4 | 3.1 |
| Polymer | 40% in Water | Cold | 79 | 89.4 | 0.2 | 80.3 | 3.1 |
| Titanium | 40% in Water | Yes | 83 | 98.5 | 1.1 | 84.9 | 2 |
| Titanium | 40% in Water | No | N.D. | 99.6 | 0 | 96.6 | 0 |
| Titanium | 40% in Water | Yes | 81 | 98.8 | 0.9 | 94.7 | 2.4 |
| Titanium | 40% in Water | No | 82 | 99.9 | 0 | 95 | 1.9 |
| Titanium | 40% in Water | Yes | 73 | 99.1 | 0.9 | 88.3 | 3 |
| Titanium | 40% in Water | Yes | 79 | 99 | 0.8 | 94.3 | 3.4 |
| Titanium | 40% in Water | Yes | 74 | 98.6 | 0.5 | 90.9 | 3.6 |

EXAMPLE 3

Long Term Accelerated Stability Studies of Leuprolide Acetate in Water

Figure 2:
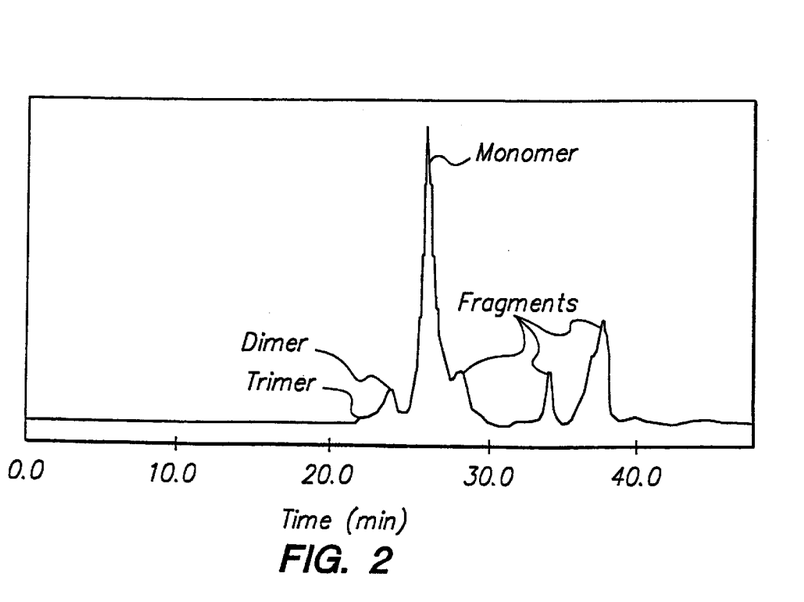
FIG. 2 shows the same sample as FIG. 1 injected by size exclusion chromatography (SEC). This figure shows that there is very little aggregation, and what aggregation there is is comprised of dimer and trimer products, with no higher order aggregation.

Solutions of 40% leuprolide acetate (w/w) in water were prepared, loaded into reservoirs, stored for two months at 80° C. and analyzed as described above. Results, shown in FIGS. 1 (RP-HPLC) and 2 (SEC) show that 81.1% leuprolide was recovered, with only 14.6% chemical degradation and 5.1 % physical aggregation after the two month period.

Figure 4:
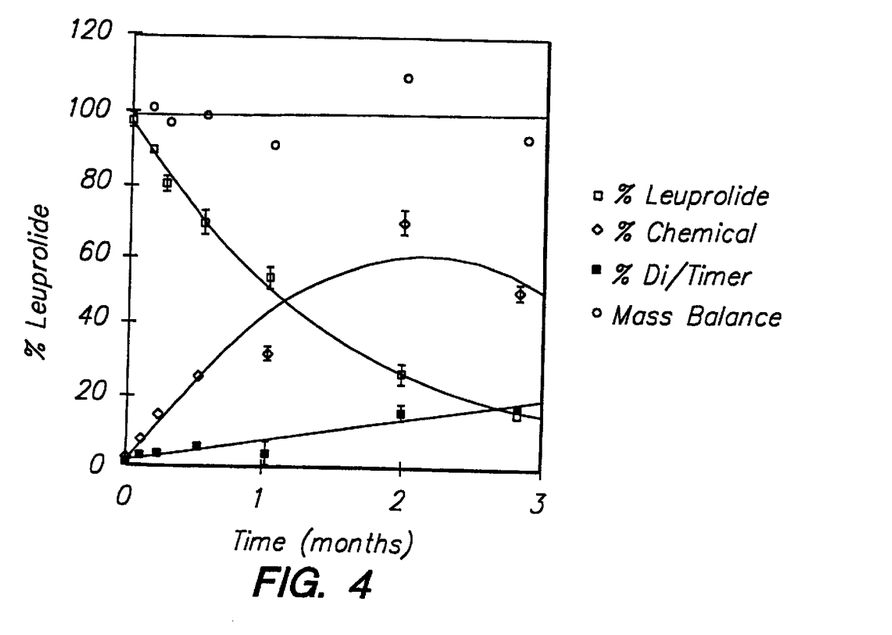
FIG. 4 illustrates the chemical and physical stability of a 40% leuprolide acetate solution in water after about three months at 80° C.

Leuprolide acetate solutions (40% (w/w) in water) were prepared, loaded, stored and analyzed as set forth above. FIG. 4 is a plot of leuprolide, and its chemical and physical degradation products recovered over a three month time period. The sum of these three elements is also presented as mass balance. The results show that we can account for all the peptide material as either intact leuprolide or a degradation species, indicating that stability studies are not missing an unknown degradation process or product.

Figure 5:
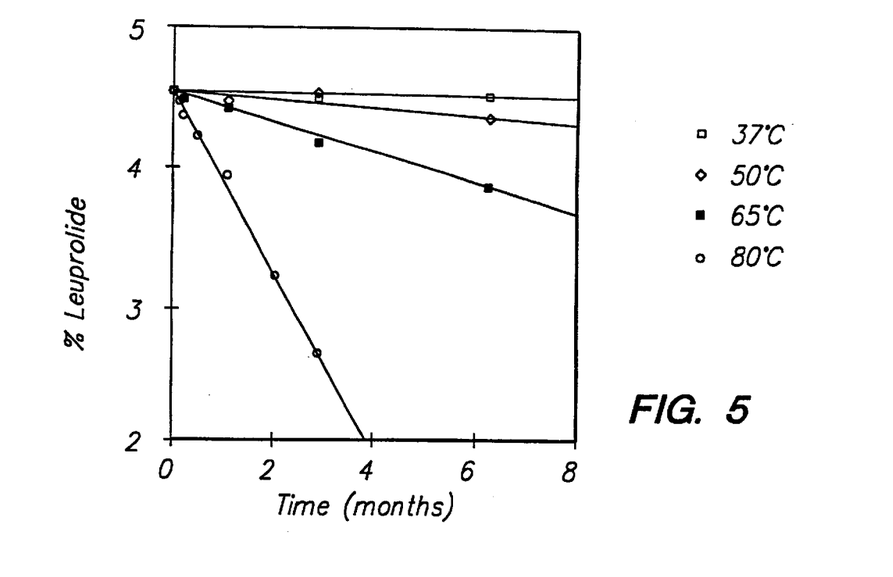
FIG. 5 illustrates the loss of leuprolide acetate fit to pseudo first order kinetics from a 40% solution in water over a period of three to six months at 37° C., 50° C., 65° C. and 80° C.

Leuprolide acetate solutions (40% (w/w) in water) were prepared, loaded, stored at 37° C., 50° C., 65° C. or 80° C. and analyzed using RP-HPLC as described above. FIG. 5 shows the loss of leuprolide from these solutions over a three to six month period, and indicates that leuprolide degradation fits pseudo first order kinetics. Furthermore, as discussed below, FIG. 3 indicates that leuprolide in water degradation fits linear Arrhenius kinetics. Therefore, accelerated stability studies are a valid technique for assessing the stability of leuprolide and extrapolating back to 37° C.

Solutions of 40% leuprolide acetate (w/w) in water were prepared, loaded into reservoirs, stored at 37° C., 50° C., 65° C. or 80° C. and analyzed using RP-HPLC as described above. Results were calculated as described in *Physical Pharmacy: Physical Chemical Principles in the Pharmaceutical Sciences,* 3rd ed., Martin et al., Chapter 14 (1983) and showed the $E_a$ of these solutions to be 22.2 kcal/mole with a $t_{90}$ of 13.8 months.

Figure 3:
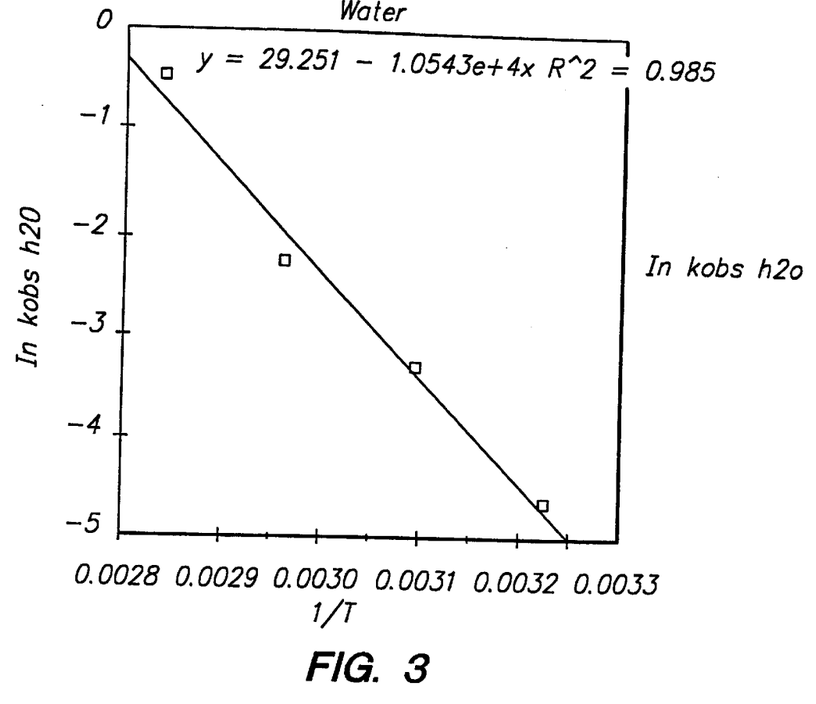
FIG. 3 presents the Arrhenius plot showing the loss of leuprolide from 40% solutions of leuprolide acetate in water.

The data are shown below and an Arrhenius plot of the data is presented in FIG. 3.

| | Water | |
|---|---|---|
| °C. | Kobs (months$^{-1}$) | $t_{1/2}$ (months) |
| 37 | 7.24 × 10$^{-3}$ | 95.7 |
| 50 | 3.21 × 10$^{-2}$ | 21.6 |
| 65 | 0.111 | 6.3 |
| 80 | 0.655 | 1.1 |

$E_a$ = 22.2 kcal/mole

EXAMPLE 4

Long Term Stability Studies of Leuprolide Acetate in Water

The chemical stability of 40% leuprolide acetate solutions prepared and analyzed as described above is presented in FIG. 6. After nine months at 37° C., more than 85% (88.3%) leuprolide was present, with less than 10% (8.4%) chemical degradation products (shown as "early" in the figure, based on the RP-HPLC profile) and less than 5% (3.5%) physical aggregates (shown as "late" in the figure, based on RP-HPLC data, but in good agreement with SEC data).

EXAMPLE 5

Accelerated Stability Studies of Goserelin

Formulations of 30% goserelin (w/w) in acetate buffer (pH 5.0, 0.0282M) with 3% mannitol were stored in glass ampules for 14 days at 80° C. and analyzed for purity as described above.

Figure 7:
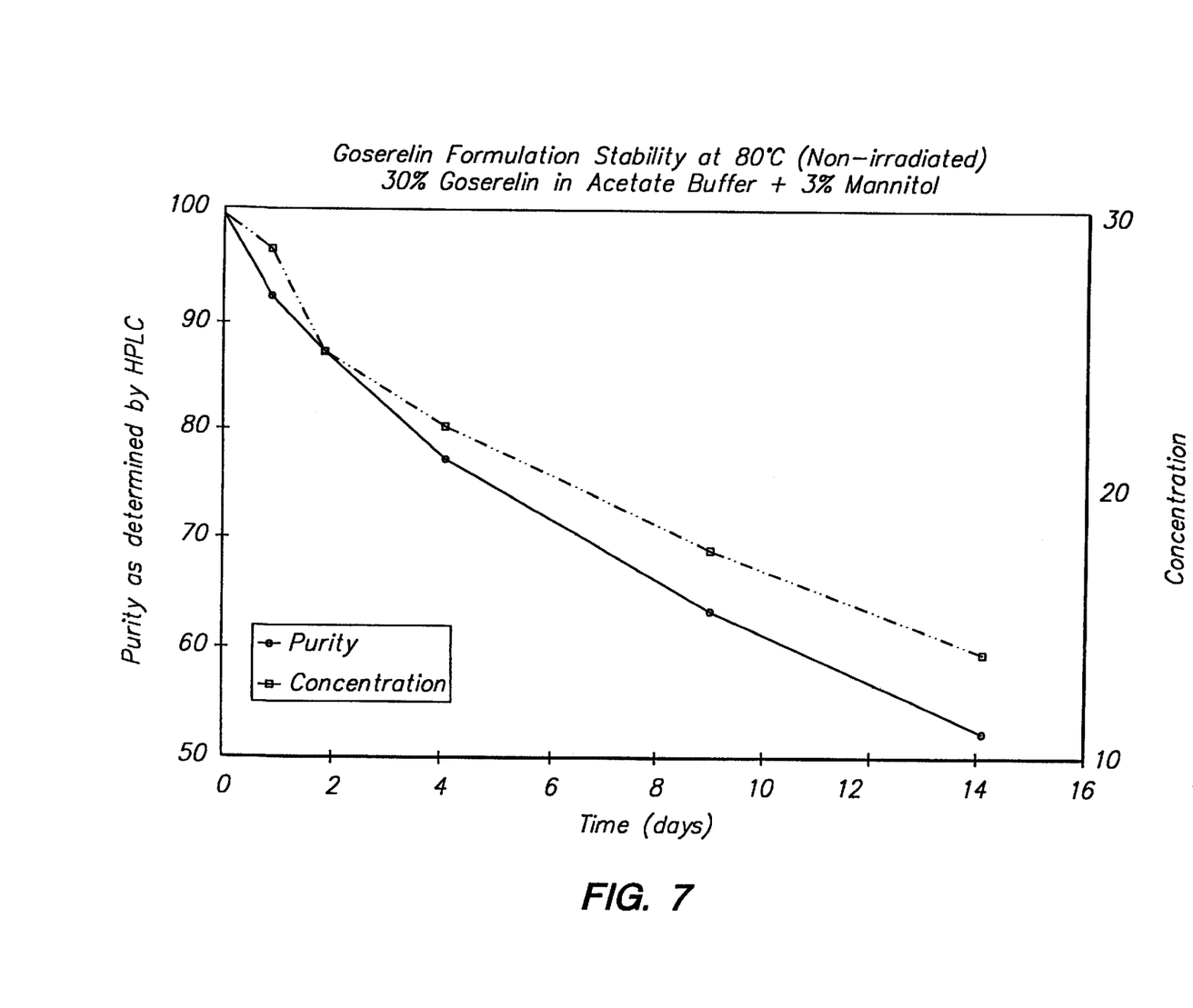
FIG. 7 illustrates the stability of a 30% goserelin solution in acetate buffer and mannitol after 14 days at 80° C.

Results in FIG. 7 show that after 9 days about 65% goserelin remained.

EXAMPLE 6

Stability Studies of Goserelin Formulations

Formulations of 40–45% (w/w) goserelin in either acetate buffer, with 3% mannitol or acetate buffer with salt (0.9% NaCl) were prepared as described above and placed in polymeric containers.

The containers were stored at 37° C. for one month in an incubator.

The samples were analyzed using RP-HPLC to determine the chemical stability of the aged formulations.

Results, presented below, demonstrate that these aqueous formulations were able to maintain the stability of the LHRH-related compound goserelin. In each case, at least 98% goserelin was retained.

| DRUG | VEHICLE | % PURITY | % CON-CENTRATION |
|---|---|---|---|
| Goserelin | Acetate Buffer/Mannitol | 98.1 | 54.2 |
| Goserelin | Acetate Buffer/Salt | 98.0 | 50.1 |

EXAMPLE 7

Stability Studies of Nafarelin Formulations

Formulations of 15% (w/w) nafarelin in acetate buffer with 3% mannitol were prepared as described above and placed in polymeric containers.

The containers were stored at 37° C. for one month in an incubator.

The samples were analyzed using RP-HPLC to determine the chemical stability of the aged formulations.

Results, presented below, demonstrate that these aqueous formulations were able to maintain the stability of the LHRH-related compound nafarelin, as at least 98% nafarelin was retained.

| DRUG | VEHICLE | % PURITY | % CON-CENTRATION |
|---|---|---|---|
| Nafarelin | Acetate Buffer/Mannitol | 98.8 | 18.3 |

Modification of the above-described modes of carrying out various embodiments of this invention will be apparent to those of skill in the art following the teachings of this invention as set forth herein. The examples described above are not limiting, but are merely exemplary of this invention, the scope of which is defined by the following claims.

What is claimed is:

1. A stable aqueous formulation of a peptide related compound comprising:
   a) at least about 10% (w/w) of at least one peptide compound; and
   b) water, wherein said formulation is stable at 37° C. for at least 2 months.

2. The formulation of claim 1 which comprises at least about 30% (w/w) peptide compound.

3. The formulation of claim 1 wherein said peptide compound is an LHRH-related compound.

4. The formulation of claim 3 wherein said peptide compound is selected from the group consisting of leuprolide, LHRH, nafarelin and goserelin.

5. The formulation of claim 1 which is stable after irradiation.

6. The formulation of claim 1 which is stable at 37° C. for at least one year.

7. The formulation of claim 1 which is adapted for use in an implantable drug delivery device.

8. The formulation of claim 1 which further comprises at least one selected from the group consisting of a buffer, an excipient, a solvent, a solubilizer and a preservative.

9. The formulation of claim 1 which consists essentially of about 30% to about 50% (w/w) of the LHRH-related compound leuprolide acetate in sterile distilled water.

10. The formulation of claim 1 which forms a gel.

11. The formulation of claim 1 further comprising at least one non-aqueous polar aprotic solvent.

12. The formulation of claim 11 wherein said non-aqueous polar aprotic solvent is DMSO or DMF.

13. A method for preparing the stable aqueous formulation of claim 1 comprising dissolving at least about 10% (w/w) of at least one peptide compound in water.

14. The method of claim 13 wherein at least about 30% (w/w) peptide compound is dissolved.

15. The method of claim 13 wherein said peptide compound is an LHRH-related compound.

16. The method of claim 15 wherein said peptide compound is selected from the group consisting of leuprolide, LHRH, nafarelin and goserelin.

17. The method of claim 13 further comprising the step of adding at least one selected from the group consisting of a buffer, an excipient, a solvent, a solubilizer and a preservative.

18. The method of claim 13 wherein about 30% to about 50% (w/w) of the LHRH-related compound leuprolide acetate is dissolved in sterile distilled water.

19. The method of claim 13 further comprising the step of adding at least one non-aqueous polar aprotic solvent.

20. The method of claim 19 wherein said non-aqueous polar aprotic solvent is DMSO or DMF.

21. A method for treating a subject suffering from a condition which may be alleviated by administration of an peptide compound comprising administering to said subject an effective amount of the formulation of claim 1.

22. The method of claim 21 wherein said administration is parenteral administration.

23. The method of claim 21 wherein said administration is long-term continuous administration.

24. The method of claim 23 wherein said administration is accomplished by use of an implantable drug delivery device.

25. The method of claim 21 wherein said condition is prostatic cancer and said peptide compound is leuprolide.

26. The method of claim 21 wherein at least about 80 micrograms of leuprolide is administered daily.

27. The method of claim 26 wherein said daily administration continues for a period selected from the group consisting of 3 months, 6 months and 12 months.

28. The method of claim 27 wherein said daily administration for said period is continuous administration accomplished using an implantable drug delivery system.

29. The method of claim 21 wherein said condition is prostatic cancer and said peptide compound is an LHRH antagonist.

30. The formulation of claim 1 which is stable at 37° C. for at least 3 months.

* * * * *